United States Patent [19]
Hibbard

[11] Patent Number: 5,599,278
[45] Date of Patent: Feb. 4, 1997

[54] AUTOCLAVABLE RIGID ENDOSCOPE

[75] Inventor: Erich M. N. Hibbard, 526 Moorings Cir., Arnold, Md. 21012

[73] Assignee: Erich M. N. Hibbard, Arnold, Md.

[21] Appl. No.: 404,576

[22] Filed: Mar. 15, 1995

Related U.S. Application Data

[63] Continuation-in-part of Ser. No. 213,276, Mar. 15, 1994, abandoned.

[51] Int. Cl.$^6$ .................................................. A61B 1/04
[52] U.S. Cl. .................................... 600/133; 600/198
[58] Field of Search ............................... 600/133, 134, 600/138, 169, 198; 348/82, 83; 359/512, 513

[56] References Cited

U.S. PATENT DOCUMENTS

| | | | |
|---|---|---|---|
| 4,779,613 | 10/1988 | Hashiguchi et al. | 128/6 |
| 4,878,485 | 11/1989 | Adair | 128/6 |
| 5,201,977 | 4/1993 | Aoshima | 156/153 |
| 5,212,595 | 5/1993 | Dennison et al. | 359/513 |
| 5,377,669 | 1/1995 | Schulz | 128/6 |
| 5,424,877 | 6/1995 | Tsuyuki et al. | 359/663 |

Primary Examiner—Richard J. Apley
Assistant Examiner—Beverly M. Flanagan
Attorney, Agent, or Firm—Senniger, Powers, Leavitt & Roedel

[57] ABSTRACT

An autoclavable endoscope having a housing, an eyepiece, an insertion tube, proximal and distal windows, and seals seal against the passage of contaminants into the endoscope during autoclaving and the housing, eyepiece, insertion tube, windows and light pipe are comprised of materials which withstand a temperature of at least about 1200° F.

21 Claims, 2 Drawing Sheets

AUTOCLAVABLE RIGID ENDOSCOPE

This application is a continuation-in-part application of U.S. Ser. No. 08/213,276 filed Mar. 15, 1994, now abandoned.

BACKGROUND OF THE INVENTION

The present invention relates generally to rigid endoscopes used in examining body cavities. The invention particularly relates to a rigid endoscope which is impermeable to liquids and vapors used in sterilization procedures and contaminants encountered during use.

Endoscopes, such as cystoscopes, arthroscopes, bronco-scopes, laparoscopes and urethroscopes, must be cleaned and sterilized after use to eliminate microorganisms and viruses on their surfaces before the instrument is used again. Numerous problems have been experienced with conventional cleaning and sterilization methods now used in the industry.

Endoscopes are typically cleaned in a glutaraldehyde solution for thirty minutes to several hours depending upon the organisms to which the scope has been exposed. In some cases, the glutaraldehyde solution has been ineffective in destroying all microbes on the endoscope, allowing subsequent patients to be exposed to the microbes. The prolonged cleaning operation also limits the amount of time in which the endoscope is available for use. Another problem associated with the cleaning solution is that it gradually deteriorates seals at the distal and proximal ends of an endoscope as it is repeatedly cleaned. After a period of usage, bodily fluids from a patient may leak through the weakened seals and contaminate the interior of the endoscope. The fluids could infect subsequent patients who are examined with the scope. Also, the cleaning solution may eventually penetrate the proximal and distal ends of the endoscope and cloud the optical lenses within the instrument. The endoscope is then inoperative because an image cannot be seen through the fogged lenses. The scope must be repaired by replacing the seals and cleaning and drying the interior of the scope so that it can be used again.

Endoscopes are often sterilized by exposing them to ethylene oxide gas for periods of up to eight hours. The lengthy sterilization process limits the time in which the endoscope is available for use. Additionally, ethylene oxide can cause serious health hazards. Ethylene oxide is an irritant and a suspected human carcinogen which may cause illness following long term exposure. It is also a safety hazard because of its high flammability. Ethylene oxide adversely affects endoscopes after repeated exposure to the gas by damaging the proximal and distal seals. Once the seals are damaged, the gas leaks into the endoscope and condenses on the optical lenses, causing them to become discolored. The ethylene oxide may also deteriorate the epoxy which holds the lenses in place. The seals and the lens system within the endoscope must be replaced before the endoscope can be used again.

Steam sterilization is recognized in the industry as the most effective sterilization technique. However, the seals of conventional endoscopes are prone to failure after frequent sterilization. The endoscopes have a variety of metals such as stainless steel, brass and chrome adjacent the seals. As an endoscope is continually heated to temperatures of up to about 325° F. by the autoclave and then cooled, the metals expand and contract at different rates because the metals have differing thermal expansion coefficients. Eventually the joints between the metals and the seals are loosened and steam permeates the interior of the endoscope, clouding the lenses and necessitating repair of the scope.

Attempts have been made at limiting the internal damage to an endoscope when the seals fail. U.S. Pat. No. 4,779,613 describes an endoscope which is said to require simple repairs if water vapor enters the interior of the endoscope because of its airtight observing optical system. The observing optical system, which extends from the objective near the distal tip to the eyepiece near the proximal end, is sealed with silicone-based or epoxy-based cements or O-rings. Although the lenses within the optical system may not be fogged by water vapor within the endoscope, the water vapor may fog the exterior of the eyepiece or the interior of the eyepiece cover glass and obstruct viewing. Even though the repairs may be simplified by the airtight optical system, repairs continue to be necessary for continued use of the endoscope.

There is a need for an autoclavable rigid endoscope that withstands repeated sterilization while remaining impervious.

SUMMARY OF THE INVENTION

It is a primary object of the present invention to provide an autoclavable rigid endoscope which is impermeable to vapors, liquids and other contaminants. In this connection, a related object of this invention is to provide an endoscope which can be used repeatedly without deterioration of its proximal and distal seals from sterilization and cleaning procedures. Other objects and advantages of the invention will be apparent from the following detailed description.

In accordance with the present invention the foregoing objectives are realized by providing an autoclavable endoscope which includes a housing defining an optical pathway therein, and a view port in the housing in optical communication with the optical pathway. An eyepiece is operatively connected to the housing adjacent the view port. The eyepiece has an opening in optical communication with the optical pathway. A transparent proximal window is adjacent the opening, and a seal between the proximal window and one of the eyepiece and the housing is all around the proximal window. The housing also includes a tube port. An elongate insertion tube extends from the tube port outward of the housing and includes a proximal end in the optical pathway and within the housing, and a distal end for insertion into a body cavity. A light port in the housing permits passage of light energy from an external source of light energy into the housing. The endoscope also includes a light pipe for transmitting light energy passing through the light port out the distal end of the insertion tube to illuminate at least a part of the body cavity. The light pipe has a first end portion in optical communication with the light port, a second end portion adjacent the distal end of the insertion tube, and an intermediate portion extending from the first end portion to the second end portion via the insertion tube. A distal window is adjacent the distal end of the insertion tube, and a seal is between the distal window and insertion tube. A sealed chamber is defined at least in part by the housing, proximal window, and distal window. The arrangement is such that the housing, eyepiece, insertion tube, the windows, and the seals seal against the passage of contaminants into or out of the sealed chamber during autoclaving of the endoscope, and the housing, eyepiece, insertion tube, windows, and light pipe withstand a temperature of at least about 1200° F.

Other objects and features will be in part apparent and in part pointed out hereinafter.

DETAILED DESCRIPTION OF THE PREFERRED EMBODIMENTS

Figure 1:
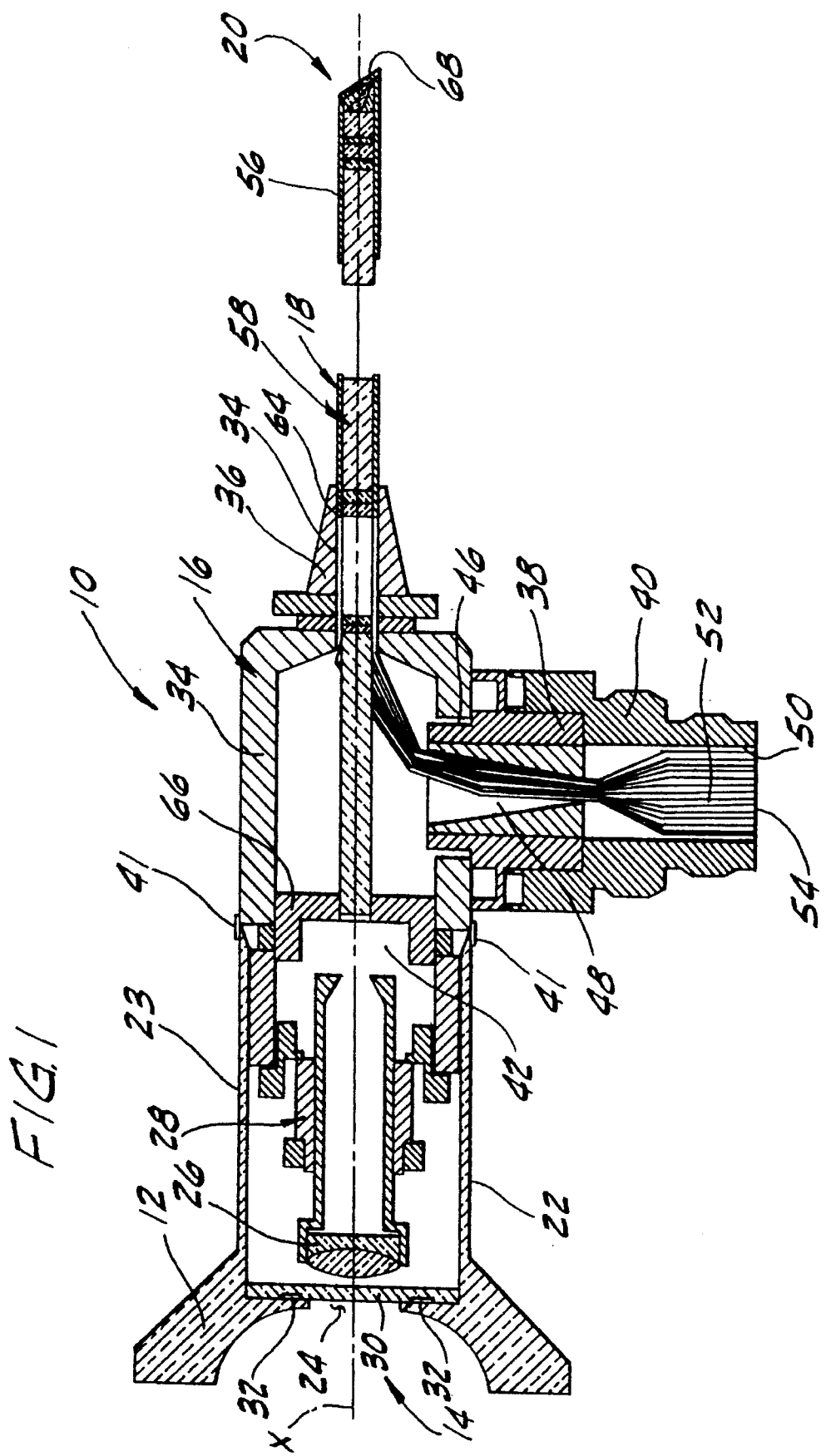
FIG. 1 is a sectional view of an endoscope of the present invention.

Turning now to FIG. 1, there is shown a rigid endoscope of the present invention generally indicated at 10. The endoscope has an eyepiece 12 at a proximal end 14 (left end as viewed in FIG. 1), a housing 16 connected to the eyepiece 12, and an insertion tube 18 extending from within the housing 16 to the distal tip 20 (right end as viewed in FIG. 1) of the endoscope 10. The endoscope is operated by inserting the insertion tube 18 into a body cavity of a patient, providing light to illuminate a portion of the cavity, and viewing the condition of the portion of the cavity through the eyepiece 12.

The eyepiece 12 has an annular portion 22 which converges to a generally cylindric portion 23. The annular portion 22 and cylindric portion 23 define an opening 24 adjacent a lens 26. The lens 26 is generally coaxial with the opening 24 and with a longitudinal axis X of the endoscope 10. The lens 26 is held in position by a conventional lens assembly indicated generally at 28. A proximal window 30 is positioned within the inner periphery of the eyepiece 12. The front surface of the proximal window 30 contacts the rear surface of the eyepiece 12 to enclose the opening 24 and protect the lens 26 from damage. A continuous annular seal 32 around the opening 24 is formed between the forward surface of the proximal window 30 and the inner surface of the eyepiece 12 to seal the proximal window 30 to the eyepiece 12, to seal against the passage of liquids, vapors and other contaminants between the eyepiece and proximal window.

The housing 16 includes an ocular housing 34, a first connector 36, a second connector 38 and a fitting 40. A seal 41 joins the eyepiece 12 to the ocular housing 34 to seal against the passage of liquids, vapors and other contaminants between the eyepiece and ocular housing. The ocular housing 34 supports the lens assembly 28 and the proximal end of the insertion tube 18. The lens 26 is held by the lens assembly 28 which is rigidly secured to the ocular housing 34 partially within a view port 42 defined by the forward-most end (left-most end as viewed in FIG. 1) of the ocular housing 34. The insertion tube 18 enters the ocular housing 34 through a passageway 44 defined by the connector 36 and the ocular housing 34. The ocular housing 34 also includes an opening 46 through which connector 38 extends to connect the fitting 40 to the ocular housing. A passageway 48 is defined by the connector 38 and the fitting 40. The fitting 40 is adopted for connection to an external source of light (not shown) and defines a light port 50. A light pipe 52 extends inward from the light port 50 through the fitting 40, into the ocular housing 34 and into the insertion tube 18. The terminal portion of the light pipe 52 is sealed by a casing 54. The light pipe of the present invention may be any optical transmission element that utilizes unfocused transmission and reflection to reduce photon losses. Preferably, however, the light pipe 52 is a fiber optic bundle comprising a plurality of individual optical fibers.

Figure 2:
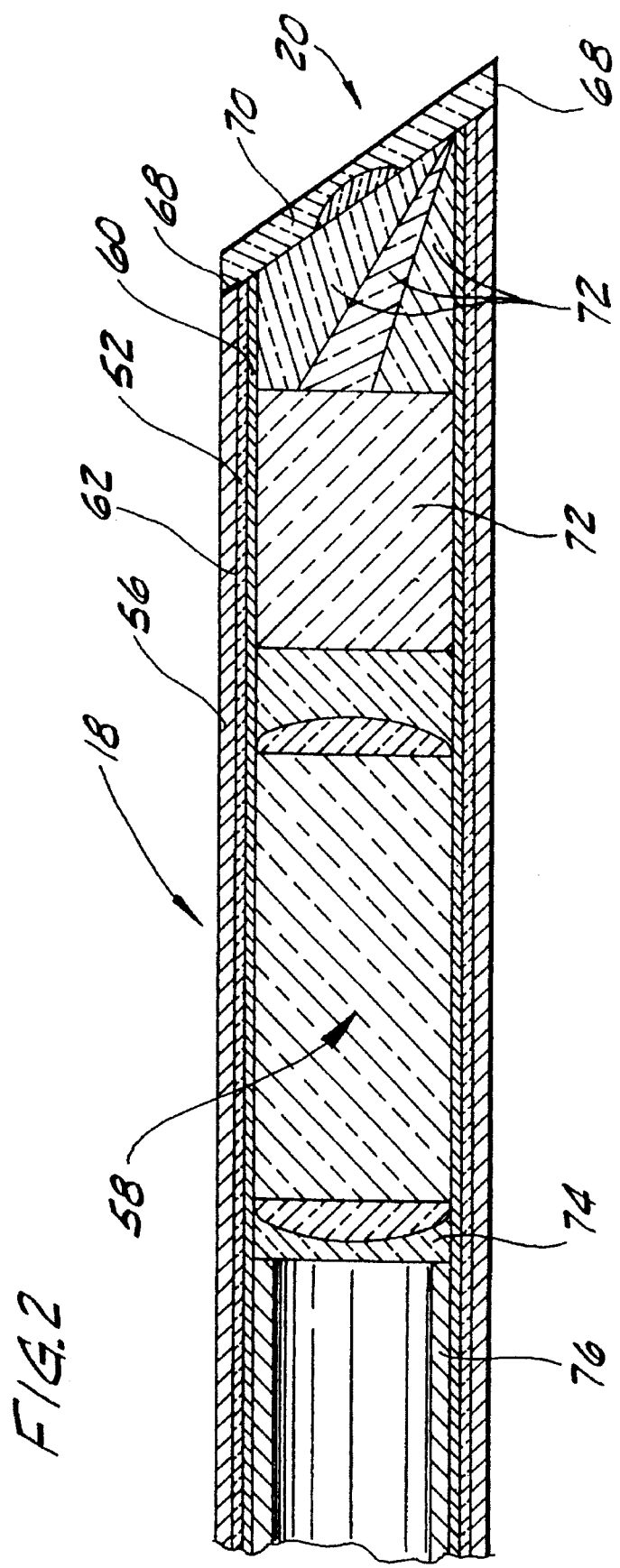
FIG. 2 is an enlarged sectional view of the distal end of the endoscope of FIG. 1.

The insertion tube 18 includes an outer cannula 56, a relay lens assembly indicated generally at 58, and an inner cannula 60 (FIG. 2). The inner cannula 60 is positioned within and coaxial to the outer cannula 56 and axis X. The inner and outer cannulas 60, 56 define an annular channel 62 (FIG. 2). The outer cannula 56 extends from a portion 64 of the passageway 44 within the connector 36 to the distal tip 20. The inner cannula 60 is held by a support 66 within the ocular housing 34 which engages the inner periphery of the ocular housing 34. The inner cannula 60 extends from within the ocular housing 34 to the distal tip 20. The light pipe 52 extends from the distal tip 20 through the channel 62 and the ocular housing 34 into the passageway 48. For example, the plurality of optical fibers illustrated in FIG. 1 are typically guided through the distal end of the channel 62, distributed evenly about the perimeter of the inner cannula 60, sealed at the distal end, and bundled together in the passageway 48 in the housing 16. A continuous annular seal 68 between the perimeter of the distal window 70 and the distal end of the outer cannula 56 seals against the passage of liquids, vapors and other contaminants between the distal window and the insertion tube. Light provided by the external light source is transmitted via the light pipe through the distal tip 20 to illuminate a portion of the body cavity for observation.

The illuminated cavity may then be observed via the relay lens assembly 58 and objective lenses 72 positioned within the inner cannula 60 adjacent the distal window 70. The relay lens assembly 58 extends within the inner cannula 60 from the objective lens 72 to the support 66. The assembly 58 may be of any conventional arrangement and includes alternating concave lenses (not shown) and achromatic lenses 74 separated by hollow, cylindrical metal spacers 76. The objective lenses 72 and the relay lens assembly 58 focus an image of an object within the body cavity so that it can be viewed through the eyepiece 12 via the lens 26.

Although a specific endoscope structure is shown in FIGS. 1 and 2, the present invention can be employed for any endoscope configuration. For example, an endoscope of the invention can have a continuous seal 32 between the proximal window 30 and the housing 16 (not shown) rather than between the window 30 and the eyepiece 12 as shown in FIG. 1. Regardless of its configuration, an endoscope constructed in accordance with the present invention is rendered autoclavable by forming the eyepiece, light pipe, and proximal and distal windows from nonexpansive, shock resistant, heat dissipating materials of high melting point, and sealing the exterior joints of the endoscope by high temperature soldering, welding, or applying a heat resistant epoxy to cover the joint.

Conventional endoscope parts are formed from metals, such as stainless steel, brass and chrome, which expand and contract differently when heated and cooled during sterilization in an autoclave. After repeated steam sterilization, the joints between the metal parts begin to loosen. Eventually, steam permeates the seals at the joints and enters the endoscope. The steam clouds the lenses, rendering the scope inoperative. Contaminants also leak into the endoscope through the loosened joints and can infect subsequent patients who are examined using the scope. Leakage is also caused when conventional epoxy seals are deteriorated by some cleaning solutions and sterilization gases. The epoxy seals also soften and deteriorate from heat generated by light travelling from the light source through the light pipe 52. Damage to the seals can result in leakage even when adjoining parts are made of the same metal.

The endoscopes of the present invention withstand repeated steam sterilization without the loosening of joints between parts of different composition. The preferred material of construction for the housing 16 and insertion tube 18 is stainless steel because it withstands autoclaving with minimum wear. The eyepiece 12 and the proximal and distal windows 30 and 70 are comprised of substantially nonexpansive materials having little or no molecular activity at the low autoclave temperatures of up to about 325° F. For purposes of the present invention, a substantially nonexpansive material has a low thermal expansion coefficient (i.e., the ratio of the change of length per unit length to the change of temperature) in comparison to brass, chrome, and stainless steel metals typically used in endoscopes. When a substantially nonexpansive material is welded, soldered, or epoxied to the housing or insertion tube, the material does not expand or contract significantly in relationship to the housing or insertion tube. The joint between the material and the housing or insertion tube does not loosen even when the housing or insertion tube is comprised of a metal which expands and contracts during steam sterilization.

The materials for use in the present invention must also have high thermal conductivity, high thermal shock resistance and a high melting point as compared to the materials used in conventional endoscopes. Generally, the materials have a melting point above 1200° F. but not greater than about 5432° F. Materials having a higher melting point can also be used in the endoscopes of the present invention. The eyepiece, light pipe, housing, insertion tube and proximal and distal windows of the endoscope of the present invention are subjected to intense heat of about 1200° F. or more when the seals at the proximal and distal ends are formed by soldering or welding. The eyepiece, light pipe and proximal and distal windows remain intact as the seals are formed because the materials dissipate heat, do not melt at welding and soldering temperatures, and withstand rapid temperature changes regardless of the thickness of the component. The housing and insertion tube are typically comprised of stainless steel which remains intact as the seals are formed. However, the glass windows of conventional endoscopes break and the glass optical fibers shatter when the proximal and distal seals are welded or soldered at elevated temperatures.

The materials for use in the present invention are also resistant to bacterial or viral growth on their surfaces and are resistant to acids used in cleaning or sterilization of an endoscope.

In addition to the above properties, the materials used in making the light pipe must be luminous for transmission of light to the distal tip. The materials for the proximal and distal windows must be optically transparent and scratch proof so that an image can be observed through the windows.

Materials having the above-described properties include fused quartz and various metallic crystals. Although the following materials are preferred, any materials having the properties defined above are suitable for use in the present invention. The eyepiece can be formed from fused quartz, sapphire, leukosapphire, ruby, silicon, aluminum-yttrium garnet, scandium oxide, tungsten, molybdenum, or niobium. Suitable materials for forming the light pipe include fused quartz, sapphire or leukosapphire. The proximal and distal windows can be formed from fused quartz, sapphire, leukosapphire, ruby, aluminum-yttrium garnet, or scandium oxide. It is preferred that the eyepiece, windows and light pipe are composed of a sapphire glass including an aluminum oxide alone or in combination with other metal oxides, carbides, nitrides, carbonitrides, borides, borates or silicates. Monocrystalline forms of sapphire, ruby, leukosapphire, aluminum-yttrium garnet and scandium oxide are more preferred than polycrystalline materials. It is most preferred that the eyepiece, light pipe and windows are composed of leukosapphire, an aluminum oxide single crystal also known as "leucosapphire." Monocrystals such as leukosapphire are commercially available from Lutch Enterprise International of Moscow, Russian Federation. The monocrystals can also be made by processes known in the art, such as those described in U.S. Pat. No. 4,915,773.

In order to safeguard a surgeon against electrical flashback caused when the surgeon strikes the shaft of the endoscope while using a cautery, the eyepiece can be composed of a material as defined above which is insulative. Alternatively, the eyepiece can be formed from any material defined above which is then externally coated with a polycarbonate thermoplastic.

The seals formed between the proximal window and the eyepiece or housing, the distal window and insertion tube, and the eyepiece and housing are formed by soldering, welding, or applying an epoxy resin. Laser welding is the preferred method of forming the seals. Two materials are welded by heating the materials to a temperature high enough to melt the materials so that they fuse to a permanent union on cooling. In order to solder two materials together for purposes of the invention, a silver alloy solder or any other solder which withstands a temperature of at least about 1200° F. is heated to a temperature high enough to melt the solder so that the solder adheres to both materials and joins them. The solder does not form an intermetallic solution with metals being joined. Two materials can also be joined by applying an epoxy resin over the joint and curing the resin at high temperature. Unlike the epoxy resins commonly used for sealing endoscopes, the epoxy resins of the present invention withstand temperatures of at least about 1200° F. The epoxied, welded, or soldered seals of the present invention are not adversely affected by the cleaning and sterilization reagents or the temperatures encountered during autoclaving. Moreover, the seals do not soften and deteriorate from heat generated as light travels through the light pipe because the light pipe rapidly dissipates heat and the seals remain intact at elevated temperatures.

While the invention is susceptible to various modifications and alternative forms, specific embodiments thereof have been shown by way of example in the drawings and have been described in detail. It should be understood, however, that it is not intended to limit the invention to the particular form disclosed, but on the contrary, the intention is to cover all modifications, equivalents and alternatives falling within the spirit and scope of the invention as defined by the appended claims.

I claim:

1. An autoclavable endoscope comprising:

a housing defining an optical pathway therein;

a view port in the housing in optical communication with the optical pathway;

an eyepiece operatively connected to the housing adjacent the view port, the eyepiece having an opening in optical communication with the optical pathway;

a transparent proximal window adjacent the opening;

a seal between the proximal window and one of the eyepiece and the housing, the seal being all around the proximal window;

a tube port in the housing;

an elongate insertion tube extending from the tube port outward of the housing, the insertion tube having a proximal end in the optical pathway and within the housing, and a distal end for insertion into a body cavity;

a light port in the housing for passage of light energy from an external source of light energy into the housing;

a light pipe for transmitting light energy passing through the light port out the distal end of the insertion tube to illuminate at least a part of the body cavity, the light pipe having a first end portion in optical communication with the light port, a second end portion adjacent the distal end of the insertion tube, and an intermediate portion extending from the first end portion to the second end portion via the insertion tube;

a distal window adjacent the distal end of the insertion tube;

a seal between the distal window and insertion tube;

a sealed chamber defined at least in part by the housing, proximal window, and distal window;

the arrangement being such that the housing, eyepiece, insertion tube, said windows, and said seals seal against the passage of contaminants into or out of the sealed chamber during autoclaving of the endoscope, and the housing, eyepiece, insertion tube, windows and light pipe are each comprised of a material which withstands a temperature of at least about 1200° F.

2. The endoscope of claim 1 wherein the material withstands a temperature ranging from about 1200° F. to about 5432° F.

3. The endoscope of claim 1 wherein said seals are formed by welding or soldering the eyepiece to the housing, the distal window to the insertion tube, and the proximal window to the eyepiece or the housing.

4. The endoscope of claim 1 wherein the light pipe comprises a fiber optic bundle.

5. The endoscope of claim 1 wherein said windows, the light pipe, and the eyepiece are comprised of a material having a low thermal expansion coefficient, a high thermal conductivity, a high thermal shock resistance, and a high melting point.

6. The endoscope of claim 5 wherein the material for the light pipe is luminous.

7. The endoscope of claim 5 wherein the material for said windows is optically transparent.

8. The endoscope of claim 5 wherein said windows, the light pipe and the eyepiece are comprised of leukosapphire.

9. The endoscope of claim 5 wherein the eyepiece is comprised of fused quartz or a crystal selected from the group consisting of sapphire, leukosapphire, ruby, silicon, aluminum-yttrium garnet, scandium oxide, tungsten, molybdenum, and niobium.

10. The endoscope of claim 6 wherein the light pipe is comprised of fused quartz or a crystal selected from the group consisting of sapphire and leukosapphire.

11. The endoscope of claim 5 wherein said windows are each comprised of fused quartz or a crystal selected from the group consisting of sapphire, leukosapphire, ruby, aluminum-yttrium garnet, and scandium oxide.

12. The endoscope of claim 9 wherein an outer surface of the eyepiece is coated with a polycarbonate.

13. The endoscope of claim 1 wherein said seals are comprised of silver solder.

14. The endoscope of claim 1 wherein said seals are formed by laser welding.

15. The endoscope of claim 1 wherein said seals are comprised of an epoxy resin that withstands a temperature of at least about 1200° F.

16. The endoscope of claim 1 wherein the housing and the insertion tube are comprised of stainless steel.

17. An autoclavable endoscope comprising:

a housing defining an optical pathway therein;

a view port in the housing in optical communication with the optical pathway;

an eyepiece operatively connected to the housing adjacent the view port, the eyepiece having an opening in optical communication with the optical pathway;

a transparent proximal window adjacent the opening;

a seal between the proximal window and one of the eyepiece and the housing, the seal being all around the proximal window;

a tube port in the housing;

an elongate insertion tube extending from the tube port outward of the housing, the insertion tube having a proximal end in the optical pathway and within the housing, and a distal end for insertion into a body cavity;

a light port in the housing for passage of light energy from an external source of light energy into the housing;

a light pipe for transmitting light energy passing through the light port out the distal end of the insertion tube to illuminate at least a part of the body cavity, the light pipe having a first end portion in optical communication with the light port, a second end portion adjacent the distal end of the insertion tube, and an intermediate portion extending from the first end portion to the second end portion via the insertion tube;

a distal window adjacent the distal end of the insertion tube;

a seal between the distal window and insertion tube;

a sealed chamber defined at least in part by the housing, proximal window, and distal window;

the arrangement being such that the housing, eyepiece, insertion tube, said windows, and said seals seal against the passage of contaminants into or out of the sealed chamber during autoclaving of the endoscope, and the eyepiece, the light pipe, and said windows are each comprised of a material having a low thermal expansion coefficient, high thermal conductivity, high thermal shock resistance, and a melting point greater than about 1200° F.

18. The endoscope of claim 17 wherein the material has a melting point which is greater than 1200° F. and less than or equal to about 5432° F.

19. The endoscope of claim 17 wherein the material for the eyepiece is fused quartz or a crystal selected from the group consisting of sapphire, leukosapphire, ruby, silicon, aluminum-yttrium garnet, scandium oxide, tungsten, molybdenum, and niobium; the material for the light pipe is fused quartz or a crystal selected from the group consisting of sapphire and leukosapphire; and the material for each of said windows is fused quartz or a crystal selected from the group consisting of sapphire, leukosapphire, ruby, aluminum-yttrium garnet, and scandium oxide.

20. An autoclavable endoscope comprising:

a housing defining an optical pathway therein;

a view port in the housing in optical communication with the optical pathway;

an eyepiece operatively connected to the housing adjacent the view port, the eyepiece having an opening in optical communication with the optical pathway;

a seal between the eyepiece and the housing;

a transparent proximal window adjacent the opening;

a seal between the proximal window and one of the eyepiece and the housing, the seal being all around the proximal window;

a tube port in the housing;

an elongate insertion tube extending from the tube port outward of the housing, the insertion tube having a proximal end in the optical pathway and within the housing, and a distal end for insertion into a body cavity;

a light port in the housing for passage of light energy from an external source of light energy into the housing;

a light pipe for transmitting light energy passing through the light port out the distal end of the insertion tube to illuminate at least a part of the body cavity, the light pipe having a first end portion in optical communication with the light port, a second end portion adjacent the distal end of the insertion tube, and an intermediate portion extending from the first end portion to the second end portion via the insertion tube;

a distal window adjacent the distal end of the insertion tube;

a seal between the distal window and insertion tube;

a sealed chamber defined at least in part by the housing, proximal window, and distal window;

the arrangement being such that the housing, eyepiece, insertion tube, said windows and said seals seal against the passage of contaminants into or out of the sealed chamber during autoclaving of the endoscope, and the eyepiece, the light pipe, said windows and said seals remain intact at a temperature of at least about 1200° F.

21. The endoscope of claim 20 wherein the eyepiece, the light pipe, said windows and said seals remain intact at a temperature ranging from about 1200° F. to about 5432° F.

* * * * *